United States Patent [19]

Ikeda et al.

[11] Patent Number: 5,665,572
[45] Date of Patent: Sep. 9, 1997

[54] POLYMERASE CHAIN REACTION AMPLIFICATION METHOD USING A SINGLE PRIMER WHICH RANDOMLY ANNEALS

[75] Inventors: Joh-E Ikeda, Ibaraki; Shinji Hadano; Haruhiko Yokoi, both of Kanagawa, all of Japan

[73] Assignee: Research Development Corporation of Japan, Tokyo, Japan

[21] Appl. No.: 294,606

[22] Filed: Aug. 23, 1994

Related U.S. Application Data

[63] Continuation of Ser. No. 936,831, Aug. 28, 1992, abandoned.

[30] Foreign Application Priority Data

Aug. 30, 1991 [JP] Japan ................. 3-220570

[51] Int. Cl.$^6$ ................. C12P 19/34; C12Q 1/68; C07H 21/02; C07H 21/04
[52] U.S. Cl. ................. 435/91.2; 435/6; 536/24.3; 536/24.31; 536/24.32; 536/24.33
[58] Field of Search ................. 435/6, 91.2; 536/24.3, 536/24.31, 24.32, 24.33

[56] References Cited

U.S. PATENT DOCUMENTS

| | | | |
|---|---|---|---|
| 4,851,331 | 7/1989 | Vary et al. | 435/6 |
| 5,043,272 | 8/1991 | Hartley | 435/91 |
| 5,262,311 | 11/1993 | Liang et al. | 436/91.2 |

OTHER PUBLICATIONS

Welsh et al, (1990), "Fingerprinting genomes using PCR with arbitrary primers", Nucleic Acids Res. 18(24):7213–7218.

Pomp et al, (1991), "Organic solvents as facilitators of polymerase chain reaction", Biotechniques 10(1):57–59.

Davis et al, (1986), "Cloning DNA from the Eukaryotic Genome: Introduction" in *Basic Methods in Molecular Biology* Elsevier Science Publishing, New York, pp. 168–170.

Perkin Elmer Cetus kit sheet, (1988), "GeneAmp DNA amplification reagent kit".

Williams et al, (1990), "DNA polymorphisms amplified by arbitrary primers are useful as genetic markers", Nucleic Acids Res. 18(22):6531–6535.

Caetano–Anolles et al, (1991), "DNA amplification fingerprinting using very short arbitrary oligonucleotide primers", Bio/Technology 9:553–557.

Liang et al, (14 Aug. 1992), "Differential display of eukaryotic messenger RNA by means of the polymerase chain reaction", Science 257:967–971.

Evans et al, "Physical mapping of complex genomes by cosmid multiplex analysis", Proc. Natl. Acad. Sci. 86:5030–5034, Jul. 1989.

Harding et al, "Genetic and physical analyses of a cluster of genes essential of xanthan gum biosynthesis in *Xanthomonas campestris*", J. Bacteriol. 169(6):2854–2861.

Gyllensten, in PCR Technology, Henry A. Erlich, ed., Stocton Press, New York, 1989, pp. 45–60, Chapter 5.

*Primary Examiner*—George C. Elliott
*Assistant Examiner*—Jeffrey Fredman
*Attorney, Agent, or Firm*—Wenderoth, Lind & Ponack

[57] ABSTRACT

A method of amplifying template DNA by polymerase chain reaction (PCR) in which a single oligonucleotide primer having a restriction site is contacted with the template DNA, whereby the oligonucleotide randomly anneals to a single strand of the template DNA and DNA sequences complementary to the single strand are synthesized. An initial PCR amplification yields synthetic DNA sequences having the oligonucleotide sequence incorporated therein at the 5' end, and a sequence complementary to the template DNA. A second PCR amplification under higher stringency conditions amplifies regions of the template DNA to give DNA fragments having the restriction sites of the oligonucleotide primer. Thereby the method can be used to amplify trace quantities of template DNA of unknown sequence simply and efficiently, which has applications in the construction of DNA libraries of chromosome specific regions and the development of probes for chromosome mapping.

5 Claims, 3 Drawing Sheets

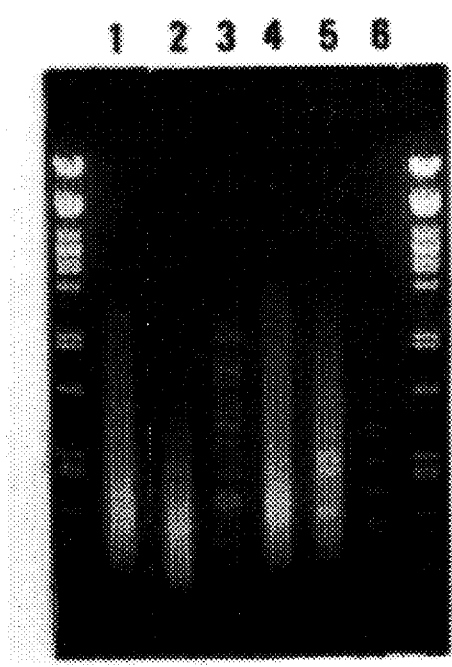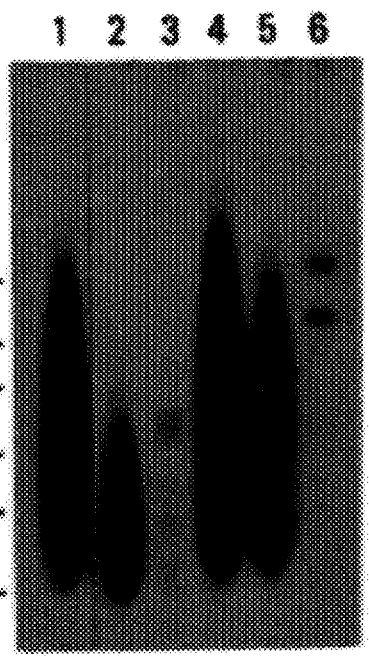

POLYMERASE CHAIN REACTION AMPLIFICATION METHOD USING A SINGLE PRIMER WHICH RANDOMLY ANNEALS

This application is a continuation of now abandoned application, Ser. No. 07/936,831, filed Aug. 28, 1992.

BACKGROUND OF THE INVENTION

1. Field of the Invention

This invention relates to a method of DNA amplification. In particular, the invention relates to an improved PCR method of DNA amplification which is useful in a wide range of medical and bio-engineering fields such as the construction of DNA libraries of specific chromosome regions, the isolation of genes originating in specified chromosome regions and probe development.

2. Description of the Related Art

In recent years, rapid progress has been made with molecular biological elucidation of the structures and mechanisms which constitute life and with the accompanying technical applications, and the foundations of genetic engineering and biotechnology have gradually been established.

Using such techniques, various genes which are characteristic of species and individual structures have been identified extending from procaryotes to eucaryotes and much knowledge has been amassed by the analysis of this genetic information. This research is now being extended to the genomic DNA of higher animals, including man.

In order to determine the base sequence of the total human genome, which is said to be composed of 3,000,000,000 base pairs, and to draw up its genetic map, the construction of DNA libraries for specific chromosome regions and the drawing up of physical maps of the chromosomes using individual DNA fragments as indicators (probes) has become an essential process. Furthermore, the physical maps of such chromosome specific regions can be an effective means of identifying the genes responsible for most human genetic diseases which have not as yet been elucidated at the molecular level and for analyzing its structure.

In the past, a chromosome DNA library has been constructed by cloning fragmented chromosomal DNA in a cloning vector, and collecting individual clones to form a library. In this way, in order to study the human genome, specific chromosome libraries constructed from sorted chromosomes or hybrid cells have been used, and, yeast artificial chromosome (YAC) libraries and the like have been prepared and used in the development of new probes for investigating the target gene.

However, in cases where such conventional gene libraries have been used it takes time to obtain the large number of necessary probes for the specific region of the chromosome and, as a result, the need for much effort, time and expense for the elucidation of the target gene cannot be avoided.

On the other hand, methods in which DNA libraries and probes have been prepared by amplifying DNA fragments of physically cut-out chromosome specific regions using the PCR (polymerase chain reaction) method have been suggested in recent years (for example, Ludecke et al., Nature, 338, 384, 1989). The PCR method involves the use of synthetic oligonucleotides complementary to certain base sequences of a template DNA as primers for in vitro DNA synthesis to enable DNA fragments which are more or less the same as template DNA to be obtained in large amounts by repeating a cycle of annealing, extension and denaturation. Automation of this amplification process has led to its application to gene cloning.

However, use of the PCR method requires prior knowledge of the base sequence at least at both ends of the template DNA fragment. Thus in cases where the method is applied to DNA fragments of unknown sequence derived from chromosome specific regions, ligation of the individual DNA fragments with vectors etc. is essential and the template DNA is accordingly subjected to various chemical and enzymic pre-treatments. Consequently, ligation PCR of this type is not only a more complicated operational procedure than the PCR method used for known DNA sequences but the amplification efficiency is also reduced and there is a disadvantage in that many DNA fragments are required for templates for example.

SUMMARY OF THE INVENTION

The present invention provides a new method of DNA amplification in which trace quantities of DNA fragments of unknown sequence can be amplified simply and efficiently.

This present invention provides a method of amplifying template DNA by the PCR reaction wherein (a) a single oligonucleotide is contacted with said template DNA whereby said oligonucleotide randomly anneals to a single strand of said template DNA. DNA sequences complementary to the said single strand are synthesized using said oligonucleotide as a primer, and said oligonucleotide also randomly anneals to the complementary strands whereby DNA sequences corresponding to the template DNA are synthesized so that PCR amplification yields synthetic DNA sequences which each incorporate said oligonucleotide sequence at the 5' end, and (b) said synthesized DNA sequences then being subjected to PCR amplification under conditions of stringency higher than in step (a).

Viewed from another aspect, the present invention provides a gene library comprising cloned sequences amplified by means of the above described method.

Furthermore, in a preferred embodiment of the DNA amplification method of the present invention the template DNA and oligonucleotide are annealed for 90–150 minutes in a reaction solution at 10°–40° C. which contains an amphipathic polymer such as polyethylene glycol etc.

BRIEF DESCRIPTION OF THE DRAWINGS

FIG. 1 is an agarose electrophoresis pattern (A) of DNA fragments amplified by the method of this present invention and a Southern blot pattern (B) in which human genome total DNA had been used as a probe.

DETAILED DESCRIPTION OF THE INVENTION

Figure 2:
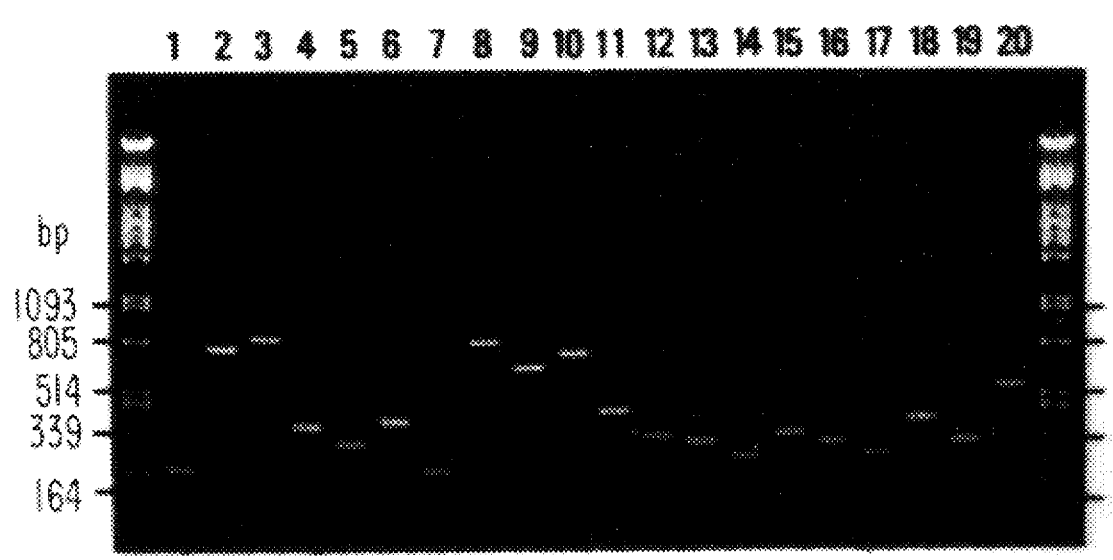
FIG. 2 is an agarose electrophoresis pattern which illustrates the insert size of the λ phage clone in which the DNA fragment amplified by the method of this present invention has been introduced.

In the present invention, the DNA sequence which is the subject of the amplification is a DNA fragment for which base sequence information has not been obtained (at least, a DNA fragment for which the base sequence information required for conventional PCR amplification has not been obtained), such as a chromosome specific region which has been physically cut out or a DNA sequence which has been cloned for a YAC library etc. for example. In the past, the ligation PCR method as described above could be used in cases where such DNA fragments were PCR amplified, but the method of this present invention is such that DNA fragments of unknown sequence can be amplified very effectively using more or less the same procedure and apparatus as used for conventional PCR without carrying out a chemical or enzymatic pre-treatment of the template DNA like that in the case of the ligation PCR method.

The method of the present invention involves first annealing a single type of oligonucleotide in an arbitrary region of a strand of the template DNA which has been thermally denatured, then extending the DNA chains which are complementary to the template DNA using this oligonucleotide as a PCR primer, and synthesizing the complementary DNA corresponding to a random sequence region of the template DNA. Thus, by repeating the cycle of denaturing, annealing and extension, various DNA sequences having the primer sequence at one end and a sequence complementary thereto at the other end thereof corresponding to a random region of the template DNA may be synthesized (this process is referred to hereinafter as low stringency PCR).

It will be appreciated that the single oligonucleotide also anneals to the complementary strand to enable PCR amplification to take place.

Low stringency PCR differs from ordinary PCR in that it uses as a primer a single oligonucleotide of which the whole sequence is unlikely to be complementary to any sequence of the template DNA. A single primer of 20–30 nucleotides which has a plurality of restriction enzyme recognition sequences and which has at least two bases on the 3'-end which do not form restriction enzyme sites may be used. Thus, since random base sequences exist in the sequence of the DNA chains, the sequence of the 3'-end of the above mentioned nucleotide can provide a PCR primer in any region of the template DNA by annealing to complementary sequences on the template DNA. Furthermore, in cases where the above mentioned oligonucleotides are used as primers, the various DNA sequences which are ultimately amplified have a plurality of restriction enzyme cleavage sites at both ends and ligation to a vector etc. can be carried out easily. The synthetic nucleotide comprised of the base sequence 5'-TAGATCTGATATCTGAATTCCC-OH3' (SEQ. ID NO. 1 referred to hereinafter as BVE22cc) can be cited as an actual example of such an oligonucleotide. BVE22cc has within the sequence comprised of 22 nucleotides recognition sequences for the restriction enzymes BgIII, EcoRV and EcoRI (AGATCT, GATATC, GAATTC respectively) and it has a continuous sequence of cytosine (C) at the 3'-end. The DNA sequence which is amplified by means of the present invention can be used directly as a probe for the screening of genome libraries for example, and in this case it is also possible to use oligonucleotides which do not include a restriction enzyme recognition sequence.

However, as mentioned above, the low stringency PCR of this present invention involves the use of an oligonucleotide of which the complementary sequence for the template DNA is small and so the efficiency of the annealing of the template DNA and the primer is low.

Thus, with the method of the present invention it is recommended that the annealing reaction of the template DNA and the oligonucleotide in the low stringency PCR is carried out over a long period of time. That is to say, whereas the annealing reaction in ordinary PCR is of the order of 1–2 minutes, in the present invention it is set at 90–150 minutes and the opportunity for the template DNA and the primer to approach and anneal is increased.

Furthermore, this annealing reaction is preferably carried out at low temperature. Ultimately, with ordinary PCR, the template DNA and the primer are annealed in a reaction solution at 50°–60° C., but in such a temperature range the free primer and template DNA in the reaction solution are subject to the effects of thermal vibration and so mutual annealing is difficult even when they approach. Hence, the temperature of the reaction solution during the annealing reaction is set to a low temperature of 10°–40° C. and the effect of thermal vibration is minimized.

Moreover, in the method of the present invention an amphipathic polymer such as polyethylene glycol (PEG) or a polysaccharide such as glucose or sucrose for example may be added in order to increase the annealing efficiency of the template DNA and the primer. Ultimately, these amphipathic polymers increase the viscosity of the reaction solution and suitably suppress the Brownian motion of the free template DNA and primer and increase the unification potential, providing conditions which are suitable for annealing. Moreover, these amphipathic polymers have no chemical action on the DNA molecule and no effect on the denaturation and extension steps in the PCR.

These means of increasing the annealing efficiency in low stringency PCR can be adopted suitably either individually or in various combinations according to the added amount and molecular weight of the oligonucleotide which is used for the primer and/or the template DNA which is the subject of the amplification for example.

Next the various DNA sequences synthesized by the low stringency PCR mentioned above are amplified without changing the sequences by means of PCR under different conditions (referred to hereinafter as high stringency PCR). In this case, the DNA sequence which is the subject of the amplification, as aforementioned, has the primer sequence at one end and its complementary sequence at the other end and so the oligonucleotide used in the low stringency PCR is used for the primer. Moreover, if the primer is of a single type and a plurality of templates (DNA sequences) is excluded, the high stringency PCR is such that template DNA is amplified according to the number of cycles in accordance with more or less the same general principles as the conventional PCR. Furthermore, the conditions for denaturation, annealing and extension can be set in the same way as for conventional PCR, or the respective conditions can be modified somewhat and carried out in a number of stages.

The various DNA sequences amplified in this way may be used as probes for genetic screening for example since they include random sequence regions of the template DNA and they are comprised of the quantities required for the various genetic operations, or they may be cloned into a vector to establish a gene library.

Such DNA sequences may be further characterized following amplification by sequencing.

EXAMPLES

Examples are described below and the DNA amplification method of the invention is described in practical terms, but of course the invention is not limited to the cases indicated below.

Moreover, in the following examples the high stringency PCR is carried out in two stages, changing the conditions, and so the low stringency PCR is indicated as the 1st PCR and the two types of high stringency PCR are indicated as the 2nd PCR and the 3rd PCR.

Example 1

Chromosome DNA recovered from two metaphase chromosome 4 50–100% fragments (ie. fragments of the distal half of the short arm of human chromosome 4) was synthesized and amplified using the method of the present invention.

First of all, for the 1st PCR, 2 μl of the 1st PCR solution was added to a tube which had been filled with 1 μl of pickup solution (composition as indicated in Table 1) which contained chromosome DNA fragments and a cycle of denaturation (90° C., 5 min), annealing (22° C., 120 min) and extension (50° C., 20 min) was repeated six times using a DNA thermal cycler (made by Perkin-Elmer-Cetus). Furthermore, at this time the temperature was raised gradually from 22° C. to 50° C. over a period of 20 minutes from annealing to extension in each cycle. Moreover, the reaction solution composition used in the 1st PCR was as shown in Table 1.

Next, after completing the 1st PCR, 6 μl of the 2nd PCR solution (same composition as in Table 1) was added to the reaction product (3 μl) to make a total of 9 μl, and the 2nd PCR was carried out by repeating the cycle of denaturation (92° C., 1.5 min), annealing (50° C., 1 min) and extension (72° C., 2 min) eleven times. However, on the first cycle only, the denaturation was carried out for 5 minutes at 92° C.

Finally, for the 3rd PCR, 51 μl of the 3rd PCR solution was added to the 2nd PCR product (9 μl) to make a total volume of 60 μl and a cycle of denaturation (92° C., 1.5 min), annealing (55° C., 1 min) and extension (72° C., 2 min) was repeated thirty times. Moreover, the composition of the 3rd PCR solution was as shown in Table 1.

This accumulation of DNA chains for which the chromosome DNA amplified by the three stage PCR was the template was analyzed using the agarose electrophoresis method and the Southern blot method using full-length human genomic DNA as a probe. Moreover, as a comparative example for this analysis, amplification with the same method as described above was also carried out with 1 pg and 10 fg of RsaI digested human genome DNA (positive control) and metaphase chromosome DNA which had been completely sublimed by laser irradiation and with no template (negative control).

The results were as shown in the agarose electrophoresis pattern (A) and the Southern blot pattern (B) of FIG. 1.

Moreover, in FIGS. 1 (A) and (B), Lane 1 shows the state of amplification of the DNA of metaphase chromosome 4 p 50–100% fragments, Lane 2 shows the state of amplification of the metaphase chromosome DNA which had been completely sublimed, Lanes 3 and 4 show the states of amplification respectively of the 1 pg and 10 fg RsaI fragments of human genome DNA, and Lane 5 shows the state of amplification in the case where no template DNA was added. Furthermore, in FIG. 1 (A), Lane 6 shows the electrophoresis pattern for the Pst I fragment of the λ phage DNA (reterred to herein after as λ/Pst I) used as a size standard.

As is clear from FIG. 1, in the method of the present invention the DNA fragment of unknown sequence cut out from the chromosome specific region (chromosome 4 p 50–100%: Lane 1) was amplified with good efficiency in the same way as the RsaI fragment of human genome DNA (Lanes 3 and 4). Moreover, the average sizes of the respective amplification products were about 500 bp for the human genome DNA fragment, and a smaller size of about 300–400 bp for the chromosome DNA fragment, implying that there is some mechanical or chemical damage during chromosome preparation. Furthermore, faint bands were obtained on amplifying the sublimed chromosome (all burned down metaphase: Lane 2) and in the absence of a template (no template: Lane 5), but these were thought to be due to inadequate sublimation treatment (laser irradiation) of the chromosome or to originate from some contamination in the manipulation process for example. In any case, there is a clear difference on comparing the amplification efficiency in the presence of the proper template DNA.

Example 2

The PCR products of the chromosome DNA obtained in Example 1 were each cloned in a λ phage vector and a library was built up.

First of all, the DNA was extracted from about half of the 3rd PCR solution in Example 1 by extraction with phenol/chloroform and chloroform/isoamyl alcohol, and by ethanol precipitation, and this DNA was treated with EcoRI to create cloning sites on both ends. After removing the very small DNA fragments by ultrafiltration, the fraction of amplified DNA (50–100 ng) was introduced and ligated to the EcoRI sites of λ phage gt11 which had been pre-treated with phosphatase and this was packaged in vitro and used to infect E. coli Y1090r cells. As a result $5 \times 10^6$ clones were obtained.

Next, 68 clones were selected randomly from this λ phage library and the inserts characterized. That is to say, the insert was amplified by means of conventional PCR taking each clone as template DNA and using a primer of the same sequence as the EcoRI part of the λ phage and the sequence adjacent thereto, and the size was analyzed by means of agarose electrophoresis.

The agarose electrophoresis patterns for 20 of the 68 types of insert analyzed are shown in FIG. 2. The results showed that the insert size of the 68 clones analyzed was distributed over about 100–1500 bp, and this is in close agreement with the size distribution of the amplified chromosome DNA in Example 1 (see FIG. 1). Furthermore, when these inserts were hybridized with human genome DNA (EcoRI or HindIII fragments), 40–60% of the clones were confirmed as being a human unique sequence, about 10% were confirmed as being a high frequency repeat sequence and 20–30% were confirmed as being a low-intermediate frequency repeat sequence.

Example 3

The optimum concentration range of the primer and/or amphipathic polymer in each PCR was tested.

10 fg of RsaI digested human genome DNA was amplified in the same way as described in Example 1. The 1st PCR was carried out with a PEG concentration of 0, 8 or 12% in the reaction solution and with a primer (BVE22cc) concentration 0.2, 0.5 or 1.0 μM. After completing six PCR series, one sixth of each reaction solution was subjected to electrophoresis on 1.5% agarose, stained with ethidium bromide and the respective reaction efficiencies were analyzed.

Figure 3:
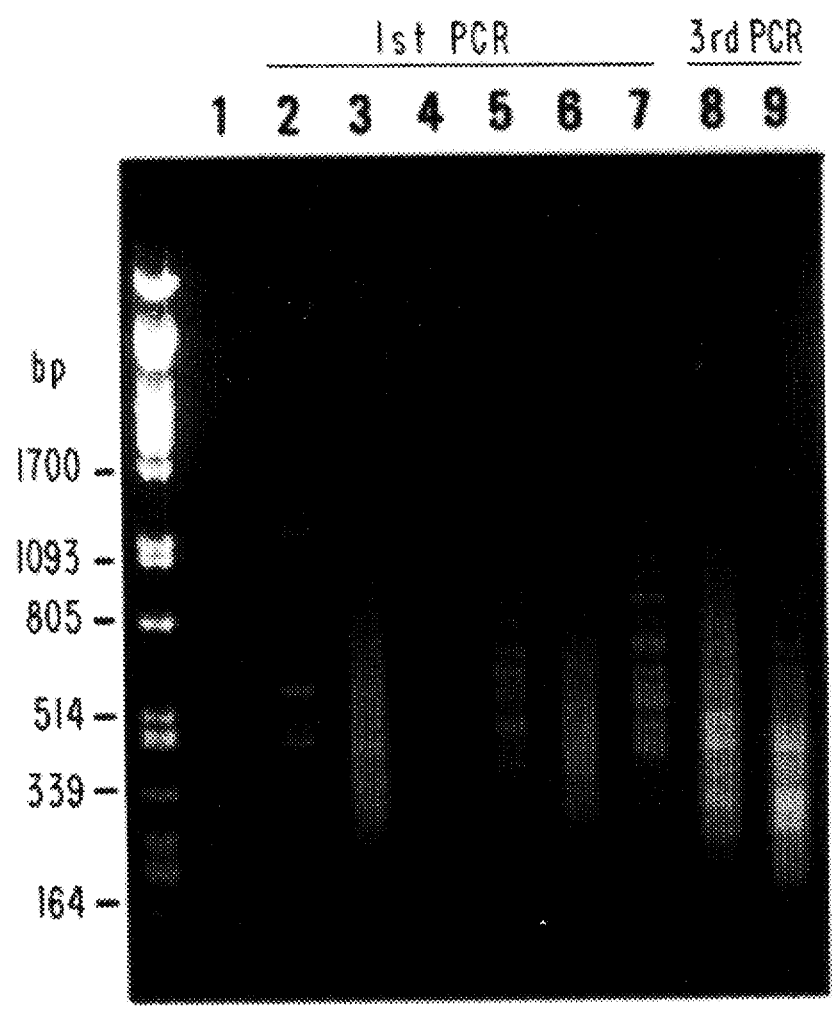
FIG. 3 is an agarose electrophoresis pattern of DNA fragments tested with the method of this present invention.

The results of this experiment were as shown in the agarose electrophoresis patterns (1st PCR) of FIG. 3. Moreover, in FIG. 3 (1st PCR), the unnumbered leftmost lane shows the λ/PstI used as a size standard, and Lanes 1–3 show the states of amplification of the DNA fragment (10 fg) with a primer concentration of 1.0 μM and PEG concentrations of 0, 8 and 12% respectively, while Lanes 4–6 show the states of amplification of the DNA fragment (10 fg) with a PEG concentration of 12% and primer concentrations of 0.2, 0.5 and 1.0 μM respectively. As is clear from FIG. 3 (1st PCR), the efficiency of the DNA chain synthesis increased as the PEG concentration was increased when the primer concentration was set at 1.0 µM (Lanes 1-3), and the efficiency of the synthesis increased as the primer concentration was increased when the PEG concentration was set at 12% (Lanes 4-6). However, although not shown in FIG. 3 the synthesis of DNA chains was also observed in cases where no template DNA was present with a PEG concentration of more than 15% or a primer concentration of more than 3 µM. Consequently, it was adjudged that when BVE22cc is used for the primer and PEG is used for the amphipathic polymer in the low stringency PCR of this present invention, a PEG concentration in the reaction solution set within the range 10-15% and a primer concentration set within the range 1.0-1.5 µM is desirable.

Next, the solution which contained 12% PEG and 1.0 µM primer from among the various reaction solutions used in the above mentioned 1st PCR was treated to a 2nd PCR using the same method as described in Example 1 and then it was submitted for a 3rd PCR. The 3rd PCR was carried out with the adjustment of the primer concentration in the reaction solution to 3.0, 4.0 or 6.0 µM.

The results obtained were as shown in FIG. 3 (3rd PCR).

Moreover, in FIG. 3 (3rd PCR), Lanes 7-9 show the states of amplification when the primer concentration was set at 3.0, 4.0 and 6.0 respectively. As is clear from FIG. 3, of the three primer concentrations tested, the amplification efficiency with 6 µM primer was the best. However DNA chains which had a smaller average size than the DNA chains synthesized at the other primer concentrations (3.0 or 4.0 µM) or in the 1st PCR (PEG 12%, primer 1.0 µM) were amplified at this concentration. Consequently, it was adjudged that in the high stringency PCR a primer concentration set to some 4.0-5.0 µM in the reaction solution in the final stage is desirable.

TABLE 1

| Reaction Solution | Composition |
| --- | --- |
| Pickup Solution | 10 mM Tris-Cl(pH 8.3), 0.1% SDS, 0.5 mg/ml$^{-1}$ Protease K |
| 1st PCR Solution | 10 mM Tris-Cl(pH 8.3), 75 mM KCl, 2.25 mM MgCl$_2$, 0.0015%(w/v)gelatin, 0.75%(v/v)Nonidet P-40, 0.75%(v/v)Tween 20, 15% Polyethylene Glycol #6000, 1.5 µM BVE22cc Primer, 300 µM each dNTPs, 0.075 unit Taq DNA Polymerase |
| 2nd PCR Solution | 10 mM Tris-Cl(pH 8.3), 50 mM KCl, 1.5 mM MgCl$_2$, 0.001% Gelatin, 200 µM each dNTPs, 0.15 unit Taq DNA Polymerase |
| 3rd PCR Solution | 10 mM Tris-Cl(pH 8.3), 50 mM KCl, 1.5 mM MgCl$_2$, 0.001% Gelatin, 4.7 µM BVE22cc Primer, 200 µM each dNTPs, 1.25 unit Taq DNT Polymerase |

We claim:

1. A method for amplifying template DNA having an unknown sequence by a polymerase chain reaction (PCR) using oligonucleotide primers comprising a contiguous sequence which consists of SEQ ID No. 1, which method comprises the steps of:
   (a) conducting multiple PCR cycles on a first reaction solution containing said template DNA, said oligonucleotide primers, and an amphipathic polymer, each PCR cycle comprising:
      (i) denaturing double-stranded DNA into single-stranded DNA, wherein in the first of said multiple PCR cycles the double-stranded DNA is said template DNA,
      (ii) annealing said oligonucleotide primers to the single-stranded DNA at 10°–40° C. for 90–150 minutes, and
      (iii) synthesizing extension products of said oligonucleotide primers, which products are complementary duplicates of Various regions of the single-stranded DNA,
   wherein the amphipathic polymer increases the annealing efficiency of the oligonucleotide primers and single-stranded DNA,
   so that a plurality of extended primer molecules are synthesized each having the nucleotide sequence of said oligonucleotide primer at both ends and a nucleotide sequence of each region of the template DNA; and
   (b) conducting multiple PCR cycles under stringency conditions higher than in step (a) on a second reaction solution containing the reaction solution produced by step (a) and an additional amount of said oligonucleotide primers, but not containing said amphipathic polymer, thereby amplifying the template DNA as a group of various DNA sequences therein.

2. The method of claim 1, wherein the amphipathic polymer is a polyethylene glycol having a molecular weight in a range of 1,000 to 10,000.

3. The method of claim 1, wherein step (a) the amphipathic polymer is polyethylene glycol present in the range of 10 to 15% and the oligonucleotide primers are present in the range of 1.0 to 1.5 µM in the first reaction solution.

4. The method of claim 1, wherein in step (b) the additional oligonucleotide primers are present in the range of 4.0 to 5.0 µM in the second reaction solution.

5. A kit for amplifying a template DNA having an unknown sequence by the method of claim 1 comprising in combination:
   (a) oligonucleotide primers comprising a contiguous sequence which consists of SEQ ID No. 1;
   (b) Tag DNA polymerase; and
   (c) nucleotide triphosphates.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

```
     ( i x ) FEATURE:
               ( A ) NAME/KEY:
               ( B ) LOCATION:
               ( C ) IDENTIFICATION METHOD:
               ( D ) OTHER INFORMATION:

( x ) PUBLICATION INFORMATION:
               ( A ) AUTHORS:
               ( B ) TITLE:
               ( C ) JOURNAL:
               ( D ) VOLUME:
               ( E ) ISSUE:
               ( F ) PAGES:
               ( G ) DATE:
               ( H ) DOCUMENT NUMBER:
               ( I ) FILING DATE:
               ( J ) PUBLICATION DATE:
               ( K ) RELEVANT RESIDUES IN SEQ ID NO:

( x i ) SEQUENCE DESCRIPTION: SEQ ID NO:1:

TAGATCTGAT ATCTGAATTC CC                                          22
```